(12) United States Patent
Guelzow et al.

(10) Patent No.: US 8,591,791 B2
(45) Date of Patent: Nov. 26, 2013

(54) METHOD OF MANUFACTURING A MICROTITRATION PLATE

(75) Inventors: Nico Guelzow, Bremen Schoenebeck (DE); Bernd Ohm Petersen, Gross Groenau (DE)

(73) Assignee: Eppendorf AG, Hamburg (DE)

( * ) Notice: Subject to any disclaimer, the term of this patent is extended or adjusted under 35 U.S.C. 154(b) by 283 days.

(21) Appl. No.: 11/936,730

(22) Filed: Nov. 7, 2007

(65) Prior Publication Data
US 2008/0084004 A1 Apr. 10, 2008

Related U.S. Application Data

(60) Division of application No. 10/894,881, filed on Jul. 20, 2004, now Pat. No. 7,347,977, which is a continuation-in-part of application No. 09/867,087, filed on May 29, 2001, now abandoned.

(30) Foreign Application Priority Data

Jun. 8, 2000 (DE) .................. 100 28 536

(51) Int. Cl.
*B29C 45/14* (2006.01)
(52) U.S. Cl.
USPC ... 264/255; 264/250; 264/328.12; 264/342 R; 264/237
(58) Field of Classification Search
None
See application file for complete search history.

(56) References Cited

U.S. PATENT DOCUMENTS

| | | | |
|---|---|---|---|
| 4,725,388 A | 2/1988 | Nelson et al. | |
| 4,743,420 A * | 5/1988 | Dutt .............................. | 264/102 |
| 5,096,672 A | 3/1992 | Tervamaki et al. | |
| 5,110,556 A | 5/1992 | Lyman et al. | |
| 5,282,543 A | 2/1994 | Picozza et al. | |
| 5,514,343 A | 5/1996 | Verwohlt et al. | |
| 5,710,381 A | 1/1998 | Atwood et al. | |
| 5,759,494 A | 6/1998 | Szlosek | |
| 5,853,894 A | 12/1998 | Brown | |
| 5,858,309 A | 1/1999 | Mathus et al. | |
| 5,948,363 A | 9/1999 | Gaillard | |
| 5,989,854 A | 11/1999 | Cook | |
| 6,015,534 A | 1/2000 | Atwood | |
| 6,051,191 A * | 4/2000 | Ireland .......................... | 422/102 |
| 6,232,114 B1 | 5/2001 | Coassin et al. | |
| 6,340,589 B1 | 1/2002 | Turner et al. | |
| 6,528,302 B2 * | 3/2003 | Turner et al. ................ | 435/288.4 |
| 6,540,965 B2 | 4/2003 | Bara | |
| 6,558,599 B1 * | 5/2003 | Bethune ........................ | 264/255 |
| 6,660,232 B1 | 12/2003 | Krueger et al. | |
| 7,347,977 B2 | 3/2008 | Guelzow et al. | |
| 2002/0074689 A1 | 6/2002 | Knebel | |

OTHER PUBLICATIONS

U.S. Appl. No. 60/145,381, filed Jul. 23, 1999, Turner, Bruce.

* cited by examiner

*Primary Examiner* — Edmund H. Lee
(74) *Attorney, Agent, or Firm* — Todd Lorenz; Arnold & Porter LLP

(57) ABSTRACT

A microtitration plate has a frame (2) made of a first stiff plastic and having a plate (4) with multiplicity of holes (2'), and a multiplicity of vessels (3) made of a second plastic suited for the PCR and/or exhibiting permeability to oxygen, which are fixedly connected to the plate (4) by directly molding them to the holes (6), which have a receiving portion (9, 10, 11) protruding from an underside (8) of the plate (4), and which are accessible from an upper surface (7) of the plate through apertures (15).

19 Claims, 6 Drawing Sheets

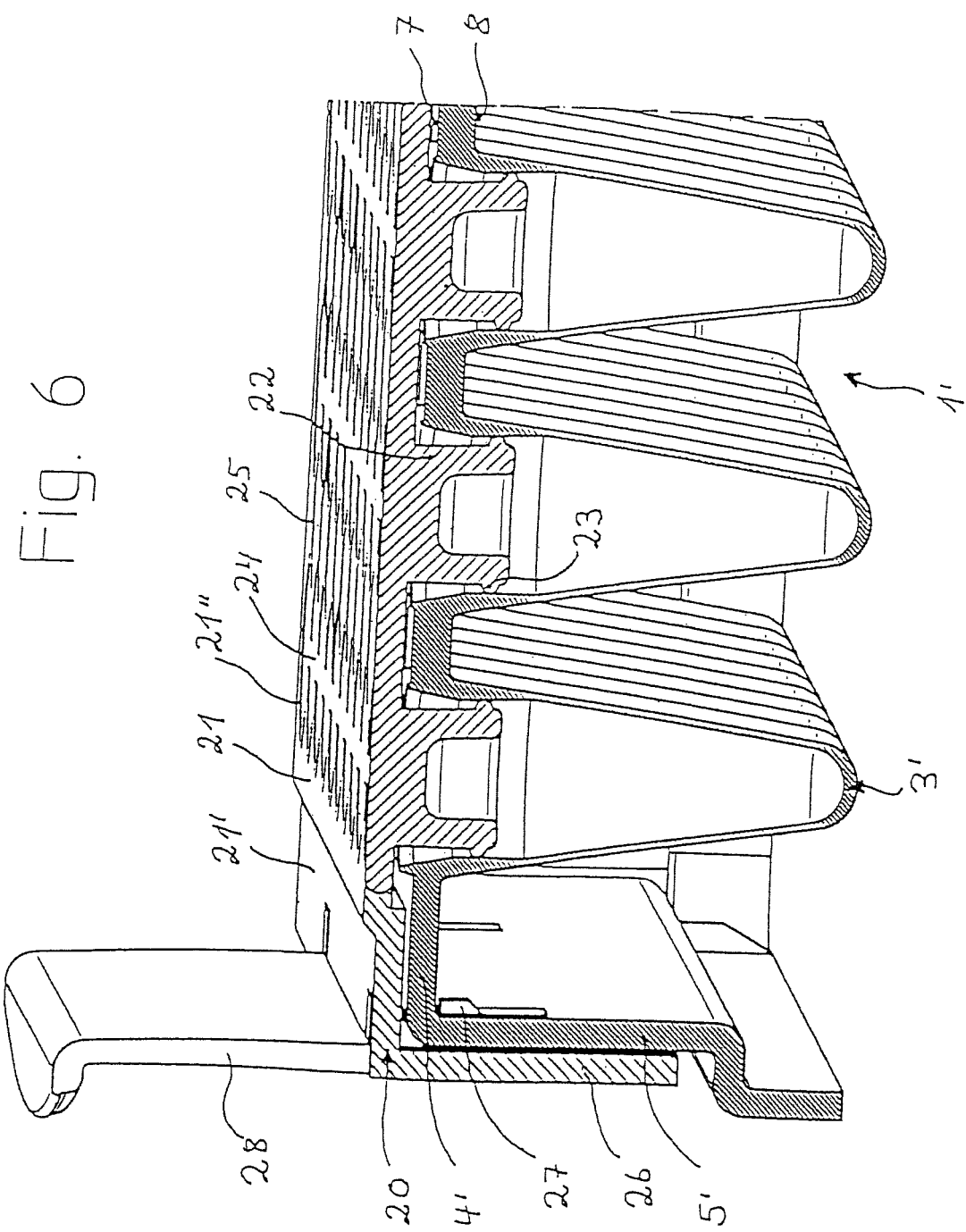

METHOD OF MANUFACTURING A MICROTITRATION PLATE

RELATED APPLICATIONS

This application is a divisional of U.S. Patent Application of U.S. patent application Ser. No. 10/894,881 filed Jul. 20, 2004 now U.S. Pat. No. 7,347,977, which is a continuation-in-part of U.S. patent application Ser. No. 09/867,087 filed May 29, 2001 now abandoned, which claims priority to German Patent Application Serial No. 100 28 536.8 filed Jun. 8, 2000.

BACKGROUND OF THE INVENTION

The present invention relates to a microtitration plate.

Microtitration plates are used for most varied microbiological, cell-breeding, and immunological techniques. In particular, microtitration plates are employed for the PCR (polymerase-chain-reaction) or the breeding of microorganisms or cells.

Microtitration plates have already been known which have a frame with a plate to which a multiplicity of vessels are fixed which have a receiving portion protruding from the underside of the plate and are accessible from the upper surface of the plate through apertures. The vessels are also referred to as "wells". The current 96-type microtitration plates have 8×12=96 vessels in rows and columns. However, microtitration plates having a larger number of vessels are used more and more.

Single-component microtitration plates in polystyrene are unsuitable for the PCR, particularly because the softening temperature of this plastic (about 85° C.) is exceeded during the PCR.

Single-component microtitration plates in polypropylene generally are adapted to be used for the PCR. However, they are flexurally soft, tend to be distorted, are uneven and are manufactured only at large tolerances and undergo large tolerance variations when in use. Specifically, they are not particularly suited for being handled by automatic devices because their softness makes it difficult for automatic devices to grip them. Further, their low dimensional stability may have the consequence that the proportioning needles will contact the walls while being introduced into the vessels. Furthermore, heat transfer into the walls is poor because the thick walls of the vessels impede it, which is adverse to temperature regulation and the length of cycle times during the PCR.

It is particularly in breeding microorganisms or cells that the sample requires sufficient oxygen supply. In the 96-type microtitration plates, this can be ensured because of the relatively large apertures of the vessels. However, in microtitration plates having a larger number of vessels, e.g. 384, oxygen-supply may be impaired very much by the reduced cross-sections of the apertures. In addition, it would be desirable to ensure oxygen supply even if the apertures are closed in order to avoid transversal contaminations between the samples of various vessels.

Attempts to avoid transversal contaminations are also made in other applications of microtitration plates. To this end, there are sealing foils which are welded onto the upper surface of the microtitration plate and have to be released again if an access is required to the contents of the vessels. In addition, there are rubber mats which have cones at their underside in order to sealingly engage the apertures of the vessels when placed on the microtitration plate. Further, there are plastic strips which are designed with stoppers at their underside in order to be forced into the apertures of a row of vessels in the microtitration plate.

The known sealing methods are complicated in use and do not satisfy the increased requirements to tightness.

Therefore, it is the object of the invention to provide a microtitration plate having more favourable characteristics in use.

In addition, a technique for the manufacture of the microtitration plate will be provided.

SUMMARY OF THE INVENTION

The object of the invention is achieved by providing a microtitration plate comprising:

a frame made of a stiff first plastic which has a plate with a multiplicity of holes, and a multiplicity of vessels made of a second plastic suited for the PCR and/or exhibiting permeability to oxygen, which are fixedly connected to the plate by directly molding them to the holes, have a receiving portion protruding from the underside of the plate, and are accessible from the upper surface of the plate through apertures, means for formlockingly connecting the vessels with the plate.

Because of its stiffness, the frame of the microtitration plate is particularly suited for being handled by automatic devices. Preferably, its edge is provided with a bordering protruding from the underside which increases its stability, may form a surface to stand on and a surface for engagement by the automatic device. For this purpose, the frame may be manufactured so as to have particularly low distortion and particularly low tolerance. The first plastic may be an amorphous plastic or even a partially crystalline, heavily filled plastic. The plastic concerned may be polycarbonate which actually is unsuited for the PCR or oxygen supply. Since this plastic is confined to the frame, however, it allows to utilize its advantageous characteristics even for microtitration plates for the PCR or oxygen supply to samples.

The vessels are made of a plastic different from that of the frame. It is a second plastic which is suitable for the PCR and/or is permeable to oxygen. Suitability for the PCR may be given, in particular, by an increased resistance to temperatures (up to about 90 to 95° C.). It may further be given by a reduced plastic affinity or neutrality of the plastic to DNA or other substances of the PCR. It preferably is a soft and/or partially crystalline plastic. Preferably, the second plastic can be polypropylene.

Each vessel is molded directly to the hole associated therewith. Generally, the vessels can be positively, formlockingly connected to the plate and/or can be non-positively, frictionally connected with the plate, and/or be connected by molding the vessels in holes having varying cross-sections in an axial direction and/or to the marginal area of the holes on at least one side of the plate, while connecting them thereto in a non-positive manner. With a vessel being molded in a hole, it becomes bonded to the plate by the material the vessel is made of. Under a formlocking connection is understood a connection in which two connected parts are provided with interengaging elements having complementary forms or shapes. Upon connection of the two parts, the interengaging complementary elements prevent the two parts from being disconnected.

Molding the vessels to the plate directly provides very short flow paths of the material in molding, which allows to achieve particularly small wall thicknesses which preferably are in the range of about 0.05 to 0.25 mm and, in particular, may be about 0.1 mm. This favors heat transfer. The vessel bottom of each vessel has a gate mark and from which the material fills the first wall portion of a reduced wall thickness and an upper wall portion connected to the plate. A gate mark is a point corresponding to a point in a mold for an injection-molded part at which a plastified plastic enters the mold. On a finished part, the gate mark is a visible as e.g., an unevenness on a surface. It is preferred that the upper wall portion be designed as a collar of an increased wall thickness, which allows to manufacture the microtitration plate with particularly small tolerances.

Since the frame is manufactured from a first plastic and the vessels are manufactured from a second plastic the best solutions possible will be achieved with materials which correspond to the desired functions of the frame and vessels. Higher rigidity, better planarity, a lower tendency to distortion, and smaller tolerances are achieved by using an amorphous, rigid, and highly temperature-resistant material for the frame. The extremely thinness of the walls for better heat transfer is achieved by molding the vessels thereto in a direct way. The frame is not filled via the vessels so that the entire pressure gradient always is available to one vessel only. The vessels may be molded of soft materials suited for the PCR. It is uncritical to mold the frame. It preferably may have several edge-side gate marks (about four to six) provided on the frame edge.

In order to ensure an increased permeability to oxygen the second plastic preferably is silicon. In particular, it may be LSR (Liquid Silicon Rubber).

According to the inventive manufacturing technique, the frame and vessels are produced by a multi-component molding technique. In the simplest case, it is a two-component molding technique or "twin-shot" technique.

For manufacture at particularly low tolerances, it is preferred to mold the frame initially and the vessels subsequently. This has the advantage that the frame first may undergo a certain shrinkage before the vessels are molded thereto. The time interval from molding the frame to molding the vessels thereto may be chosen so that the shrinkage of the frame (by cooling it down) essentially is effected completely. Once the vessels are molded on, shrinking techniques virtually do not impair the dimensional stability of the microtitration plate any longer. It specifically is the tolerance of the vessel-to-vessel distance which, thus, can be confined to very low values (about t 0.15 mm). This makes it easier to introduce proportioning needles with no wall contact.

It is particularly advantageous here if the upper wall region of the vessels is designed as a collar of an increased wall thickness because the collar may compensate hole position tolerances that have remained during molding.

The object further is achieved by providing a microtitration plate which comprises:

a rigid frame which includes a plate, a multiplicity of vessels, which are fixedly connected to the plate, have a receiving portion protruding from the underside of the plate, and are accessible from the upper surface of the plate through apertures, a rigid lid adapted to be releasably attached on the upper surface of the plate, and at least one seal between the lid and the plate which is of an elastic material which deviates from the plastic of the plate and/or the lid and is fixedly connected to the lid and/or the plate in order to close the apertures when the lid is disposed on the plate.

In other words, according to the invention, the plate and/or the lid is designed with at least one seal of an elastic material deviating from the material of the plate and/or the lid. In particular, the material concerned may be a thermoplastic, elastomer, thermoplastic elastomer or rubber. The connection of the seal to the plate and/or the lid may be a non-positive and/or positive and/or by the material of the vessel when the vessel is bonded to the plate. Thermoplastic elastomers, in particular, enable a non-positive connection with matching materials of the plate and lid. In particular, in a microtitration plate, the seal may be provided on a collar of the vessels. If the vessels are manufactured from an elastic material, there is a possibility of forming the seals integrally with the vessels here.

In this microtitration plate, the at least one integrated sealing, in conjunction with a rigid lid, makes possible rapid and simple sealing of the apertures which satisfies the high requirements to tightness. It is particularly advantageous for handling and sealing that the lid is designed so as to be adapted to be locked with the frame, specifically by locking it with the marginal area of the frame. Specifically if designed with a plane seal at its underside, the lid can also be used with known microtitration plates having thermoplastic sealing collars at the apertures of the vessels.

If the at least one seal is to be connected to the plate annular contours enclosing the apertures are preferred. If connected to the lid, the seals particularly may be annular, plug-shaped, mat-shaped or lip-shaped seals.

For the manufacture of this microtitration plate, it again is a multi-component molding technique which preferably is employed, particularly a two-component molding technique (a "twin-shot" technique) or a three-component molding technique (a "three-shot" technique. A three-component molding technique may be employed particularly if two different plastics are used for the frame and vessels, and a third plastic is employed for the at least one seal.

It is preferred that the frame be molded initially and the at least one seal is molded to the frame subsequently and/or the lid is molded initially and the at least one seal is molded to the lid subsequently. If required, the frame is molded integrally with the vessels. However, the vessels may be molded in a second step and the at least one sealing in a third step.

BRIEF DESCRIPTION OF THE DRAWINGS

The invention will now be explained in more detail with reference to the accompanying drawings of embodiments. In the drawings:

FIG. 6 shows a microtitration plate having a lid with integrated plug-shaped sealings in a partial perspective view.

DETAILED DESCRIPTION OF THE PREFERRED EMBODIMENTS

Figure 1:
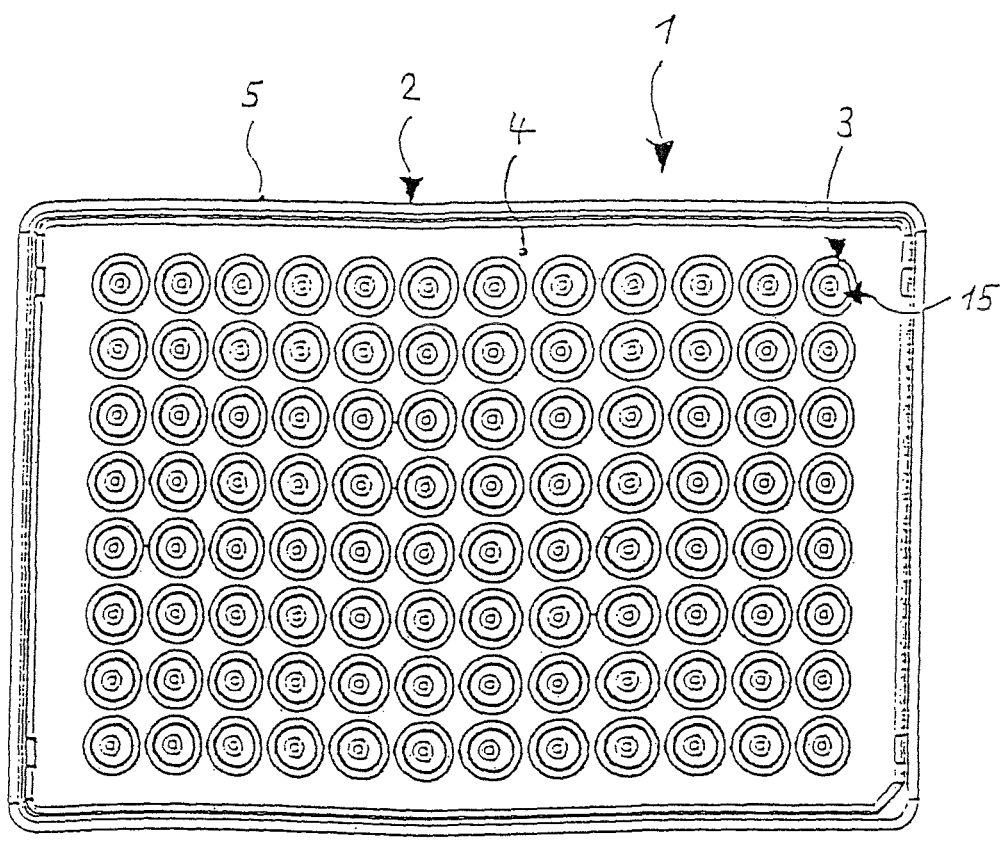
FIG. 1 shows a 96 type microtitration plate with a frame and vessels made of various plastics in a plan view.

In the drawings, the same elements are designated by identical reference numerals. The description pertaining thereto applies to all of the embodiments.

Figure 2:
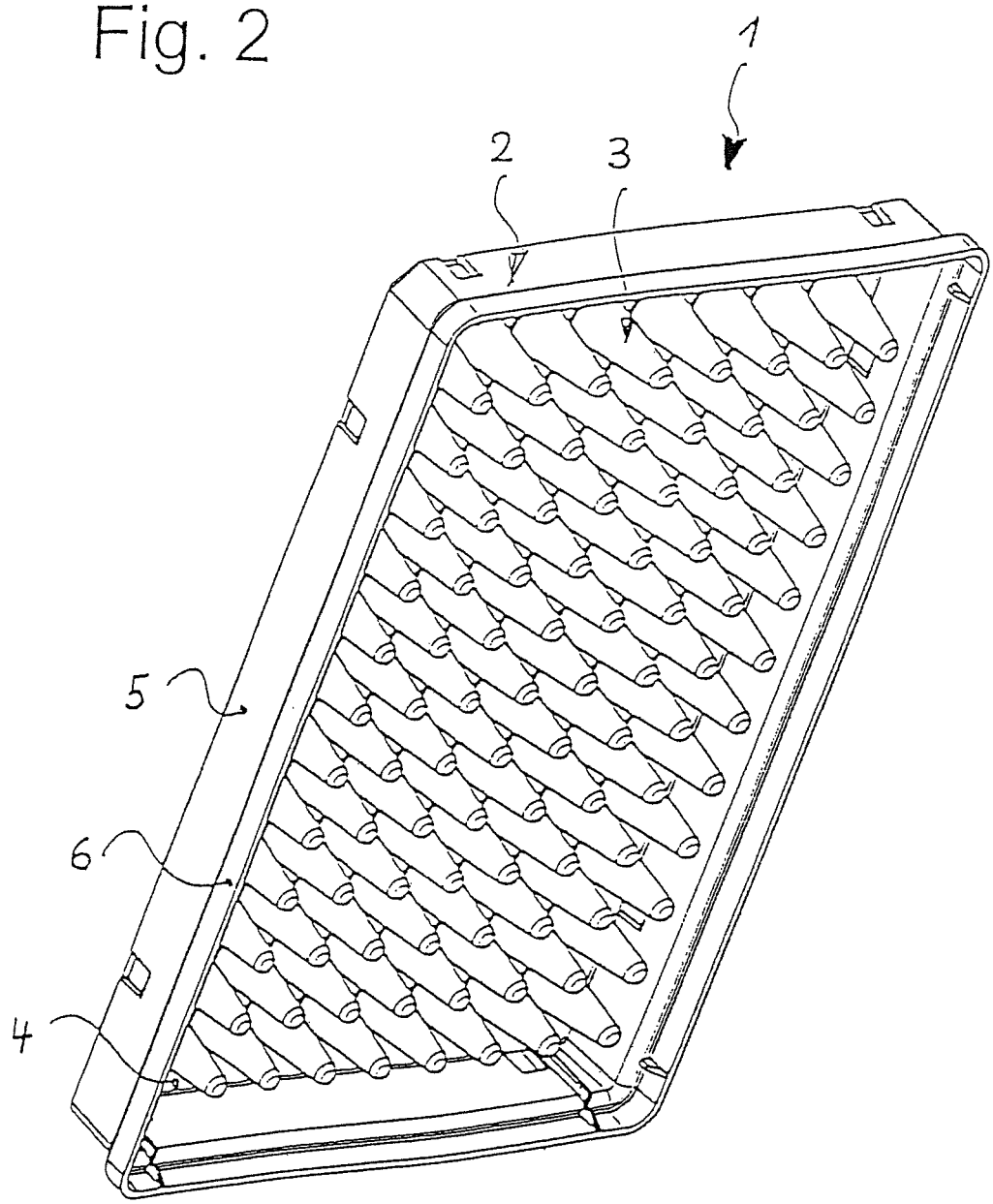
FIG. 2 shows the same microtitration plate in an oblique perspective view from bottom.
Figure 3:
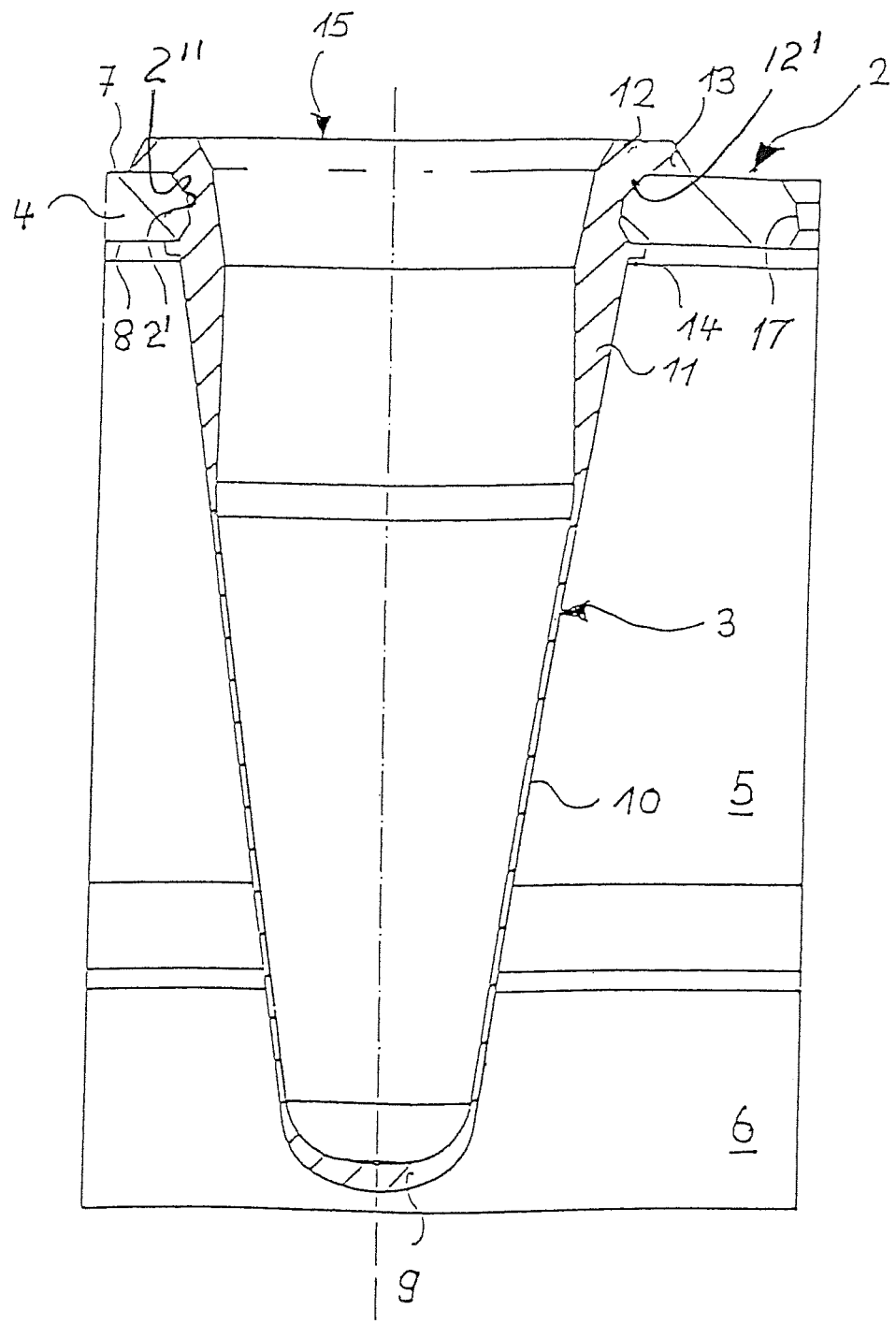
FIG. 3 shows the same microtitration plate in a largely magnified vertical section-in-part through the plate of the frame and a vessel.

Referring to FIGS. 1 through 3, a microtitration plate 1 comprises a frame 2 and a multiplicity of vessels 3. There is a total of 96 vessels arranged in eight columns and twelve rows.

The frame 2 has a substantially rectangular plate 4 the outer edge of which is surrounded by a bordering 5 which protrudes approximately perpendicular from the underside of the plate 4, i.e. beyond the vessels 3. At bottom, the bordering 5, as is known, has an expansion 6 which enables stacking on the upper surface of an appropriate microtitration plate 1.

The frame 2 has a total of ninety-six holes 2' in the plate 4. These have a profile 2" of the cross-section which widens towards the upper surface 7 of the plate 4 in two portions of different conicity and towards the underside 8 of the plate 4 in a conical portion.

In a first molding step, the frame 2 is integrally molded from a plastic which is relatively rigid when cured. Gate marks are formed at the edge of frame 2, e.g. at the lower edge of the bordering 5.

At their base, vessels 3 have a cup-shaped bottom 9 which is bordered by a conical wall portion 10 of a very small wall thickness (about 0.1 mm). Above it, there is a wall portion 1 the wall thickness of which gradually increases towards the top. At its outside, it has the same conicity as the wall portion 10. At its inside, however, it is designed nearly cylindrically, which results in an approximately wedge-shaped profile of the cross-section.

Wall portion 11 terminates in a collar 12 which also is of a largely increased wall thickness with respect to wall portion 10. Vessels 3 are molded to plate 4 in the area of collar 12. To this end, a collar 12 externally bears against the inner periphery of holes 2'. It further has a projection 13, 14 at the upper surface 7 and the underside 8 of plate 4, respectively. With the engagement of the projections 13, 14 with the upper surface 7 and the underside 8, a formlocking connection of the collar 12 and, thereby, of the vessel 3 with plate 4 is formed.

As shown in FIG. 3, the collar 12 has an outer profile 12' of the cross-section that widens likewise as the profile 2" of the hold 1', toward the upper surface 7 of the plate 4 in two portions of different conicity and toward the underside 8 of the plate 4 in a conical portion, i.e., the cross-sectional profile 2" of the hole 2' and the cross-sectional profile 12' of the collar 12 are complementarily formed. Therefore, a form locking connection is already formed when a vessel 3 is inserted in the hole 2'. The projections 13, 14 only inhance the already formed form locking connection. The collar 12 can have not two but only one projection 13 or 14. Both projections are necessary when the complementary profiles of the vessel 3 and the hole 2' have a circular cross-section.

Though a specific cross-sectional profile of the hole 2' and the vessel 3 was described, it should be understood that they can have a different shape, e.g. the hole wall can have a convex profile, with the outer surface of the collar having a concave profile. Further, the complementary profiles of the hole 2' and the vessel 3 can be formed of two sections, a cylindrical section and a conical section widening to the upper surface 7 of the plate 4 or to the underside 8. In case the conical section widens toward the upper surface 7 of the plate 4, the collar 12 is provided with a bottom projection 14. If the comical section widens to the underside 8 of the plate 4, the collar is provided with the upper projection 13.

In the area of collar 12, vessels 3 have a cross-section expanding towards the top in two portions of different conicity. Vessels are accessible from the upper surface of plate 4 through apertures 15.

All of the vessels are simultaneously molded directly to the frame 2 and the holes 2' thereof. Each vessel 3 has its own central gate mark at the underside of bottom 9. This helps achieve shorter flow paths of the plastic which are made possible by the particularly small wall thickness in wall portion 10. The material used is polypropylen or LSR, for example, for the purpose of the PCR or oxygen supply to a sample inside the vessel.

Figure 4:
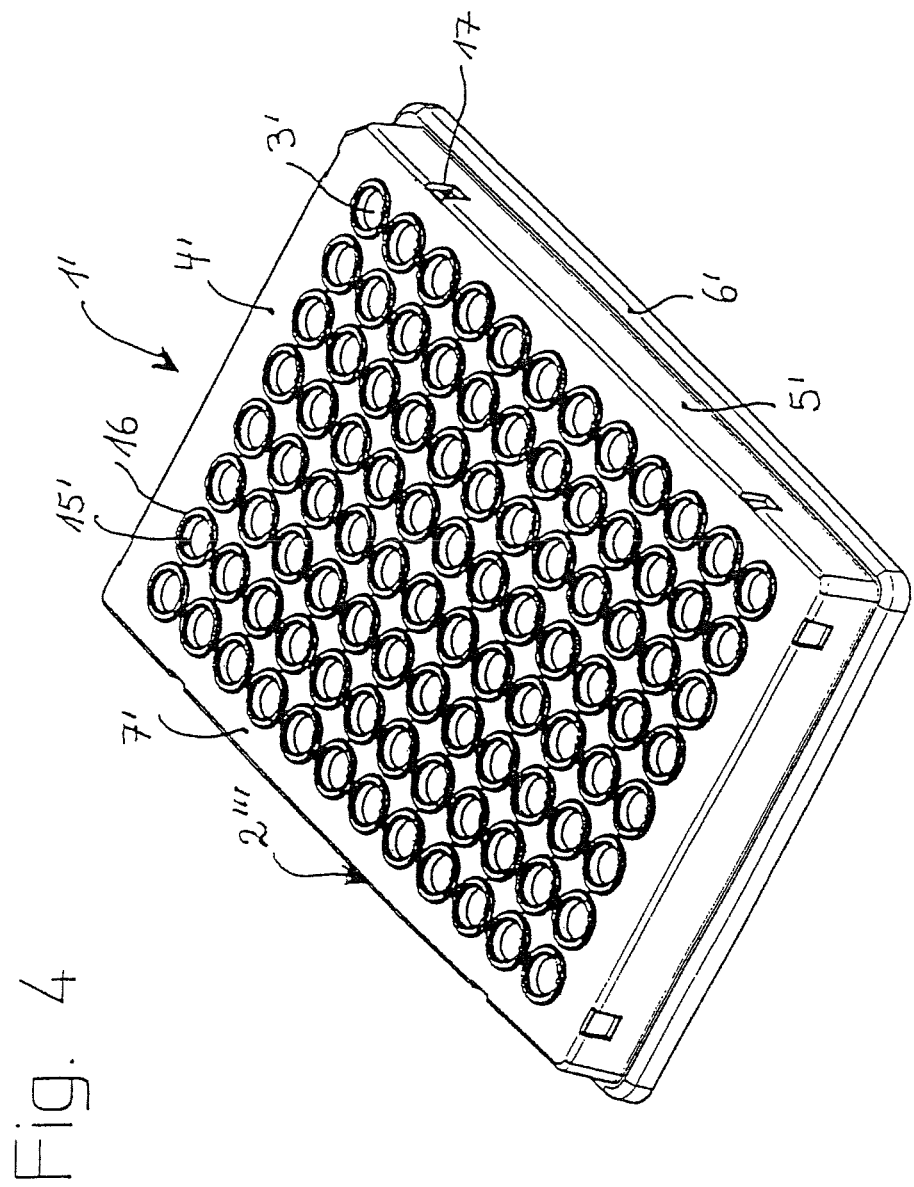
FIG. 4 shows a 96 type microtitration plate which is integrally made from a single plastic and has integrated annular sealings in an oblique perspective view from top.

FIG. 4 shows a microtitration plate 1' in which the frame 2" and the vessels 3' are integrally made of a single plastic in a known manner. The outer shape of microtitration plate 1' substantially corresponds to that of the preceding example with the vessels 3', however, having a substantially uniform course of wall thickness and are fused to plate 4' with no projections. At the edge, plate 4' is connected, in a known manner, to bordering 5' which has the expansion 6' at the bottom.

Vessels 3' are accessible from the top through apertures 15' with an annular sealing 16 made of an elastic material being disposed around each aperture. In the example, it is a plastic which is capable of getting connected to the plastic of microtitration plate 1' by being bonded thereto.

Instead, a non-positive connection may be produced by placing seal 16 in an undercut groove in the upper surface of plate 4'.

Preferably, seals 16 are fixedly connected to microtitration plate 1' by a multicomponent molding technique.

Now, it is possible to sealingly close apertures 15' by placing thereon a lid (not shown) made of a rigid material. The lid may approximately have the dimensions of plate 4'. Preferably, it is locked in the marginal area of microtitration plate 1'. Such locking may be effected, for example, in the recesses 17 which the bordering 5' has directly beneath plate 4'.

Figure 5:
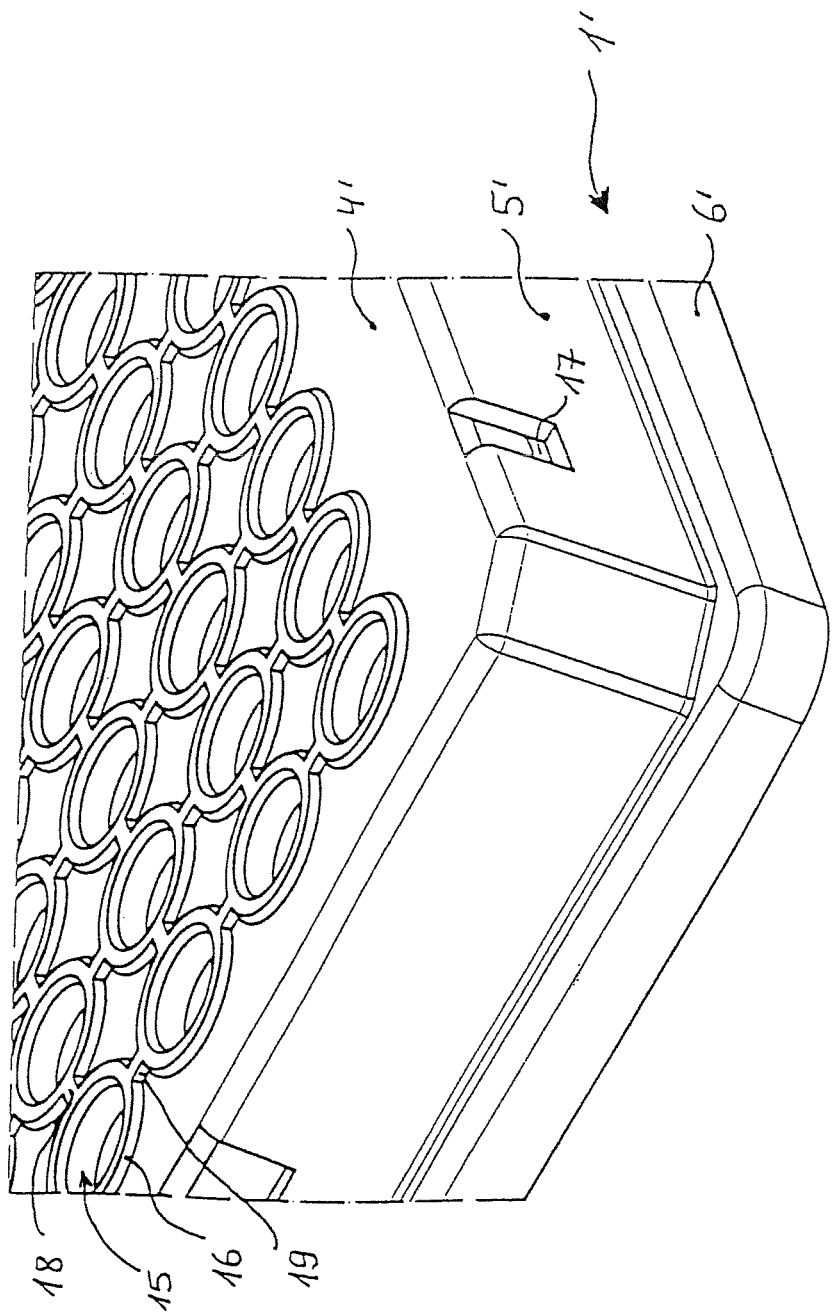
FIG. 5 shows a microtitration plate modified by connection webs between the sealings as compared to the embodiment of FIG. 4 in an oblique partial perspective view from top.

The embodiment of FIG. 5 differs from the aforementioned in that the adjoining annular seals 16 are connected to each other by straight-lined webs 18, 19 which extend in the row and column directions. This may be advantageous particularly for technical reasons of manufacture, but also for reasons of fixedly connecting the seals to the microtitration plate 1' or for providing additional sealing.

Referring to FIG. 6, a microtitration plate 1' is shown which is made of a single material only in correspondence to the one of FIG. 4. However, there are no annular seals 16 here. Plate 4' of microtitration plate 1' has seated thereon a lid 20. It has a plate 21 the contours of which substantially are the same as those of the plate 4'. Plate 21 is supported on the upper surface of plate 4' in marginal areas 21'. It is spaced by a small gap from plate 4' in a region 21" between marginal areas 21'. This allows it to be placed onto conventional microtitration plates which have sealing collars at the upper surface of retaining plate 4'.

In region 21", plate 21 has plug-like seals 22 which protrude from its underside. These plug-like seals 22 have a circumferential sealing bulge 23 at their outer periphery.

Each aperture 15' of vessels 3' has associated thereto a seal 22. Here, seals 22 engage apertures 15' so as to sealingly cause their sealing bulges 23 to bear against the inner wall of vessels 3'.

Seals 22 are disposed in appropriate recesses of plate 21. They are connected to each other by short webs 24, 25 which extend in the row and column directions.

Borderings 26 protrude from the underside of the plate at the edge thereof, from which borderings catch projections 27 protrude inwardly which are adapted to be locked in the recesses 17 (see FIG. 4) of microtitration plate 1'. Handles 28 project upwardly from borderings 26. Those make it easier for lid 20 to be locked. Furthermore, pivoting the handles 28 makes it possible to disconnect the locking engagement between catch projections 27 and recesses 17 because the borderings 26 will be pivoted along.

Preferably, lid 21 with seals 22 is also manufactured by a multi-component molding technique.

What is claimed is:

1. A method for manufacturing a microtitration plate, comprising:
a frame (2) made of a first stiff plastic which has a plate (4) with a multiplicity of holes (2') and a multiplicity of conical vessels (3) made of a second plastic which is suited for the PCR with regard to its softening temperature and/or is a silicone, which are fixedly connected to the plate (4) by being directly molded to the holes (2'), have a receiving portion (9, 10, 11) protruding from the lower side (8) of the plate (4), and are accessible from the upper surface (7) of the plate through apertures (15),
wherein the frame (2) and the vessels (3) are manufactured by a multi-component molding technique in which the frame (2) is molded first and the vessels (3) are molded subsequently, and in which the vessels (3) are molded each from a central molding point of their own, starting from their bottom (9).

2. The method according to claim 1, wherein the vessels (3) are molded at an interval from the molding of the frame (2) as substantially ensures the shrinking of the frame (2) completely before the vessels (3) are molded thereto.

3. A method for manufacturing a microtitration plate, comprising:
a frame (2) made of a first stiff plastic which has a plate (4) with a multiplicity of holes (2'), a multiplicity of conical vessels (3) made of a second plastic which is suited for the PCR with regard to its softening temperature and/or is a silicone, which are fixedly connected to the plate (4) by being directly molded to the holes (2'), have a receiving portion (9, 10, 11) protruding from the lower side (8) of the plate (4), and are accessible from the upper surface (7) of the plate through apertures (15),
wherein the frame (2) and the vessels (3) are manufactured in a multi-component molding technique in which the frame (2) is molded first and the vessels (3) are molded subsequently, and in which the vessels (3) are molded at an interval from the molding of the frame (2) as substantially ensures the shrinking of the frame (2) completely before the vessels (3) are molded thereto.

4. A method according to claim 3 wherein the vessels (3) are molded each from a central molding point of their own, starting from their bottom (9).

5. A method according to any one of claims 1-4 wherein the frame (2) is molded from several molding points in the marginal area.

6. A process for the manufacture of a microtitration plate comprising:
a frame (2) made of a stiff first plastic which has a plate (4) with a multiplicity of holes (2'), and a multiplicity of conical vessels (3) made of a second plastic suited for the PCR and/or exhibiting permeability to oxygen, which are fixedly connected to the plate (4) by directly molding them to the holes (2'), have a receiving portion (9, 10, 11) protruding from the underside (8) of the plate (4), and are accessible from the upper surface (7) of the plate through apertures (15);
wherein the frame (2) and the vessels (3) are manufactured in a multi-component molding technique; and
wherein the vessels (3) are molded from their own central molding point each, starting from their bottom (9).

7. The process according to claim 6 wherein the frame (2) is molded initially and the vessels (3) are molded subsequently.

8. The process according to claim 6 or 7 wherein the vessels (3) are molded at such interval from the molding of the frame (2) as substantially ensures the shrinking of the frame (2) completely before the vessels (3) are molded thereto.

9. The process according to claim 7 wherein the frame (2) is molded from several molding points in the marginal area.

10. A process for the manufacture of a microtitration plate, said plate comprising a frame (2) made of a stiff first plastic which has a plate (4) with a multiplicity of holes (2'), and a multiplicity of conical vessels (3) made of a second plastic suited for the PCR and/or exhibiting permeability to oxygen, which are fixedly connected to the plate (4) by directly molding them to the holes (2'), have a receiving portion (9, 10, 11) protruding from the underside (8) of the plate (4), and are accessible from the upper surface (7) of the plate through apertures (15);
wherein the frame (2) and the vessels (3) are manufactured in a multi-component molding technique;
wherein the vessels (3) are molded at such interval from the molding of the frame (2) as substantially ensures the shrinking of the frame (2) completely before the vessels (3) are molded thereto.

11. The process according to claim 10 wherein the vessels (3) are molded each from a central molding point of their own, starting from their bottom (9).

12. The method of claim 1, wherein the vessels have wall thicknesses of about 0.05 to about 0.25 mm.

13. The method of claim 12, wherein the vessels have wall thicknesses of about 0.1 mm.

14. The method of claim 3, wherein the vessels have wall thicknesses of about 0.05 mm to about 0.25 mm.

15. The method of claim 14, wherein the vessels have wall thicknesses of about 0.1 mm.

16. The process of claim 6, wherein the vessels have wall thicknesses of about 0.05 mm to about 0.25 mm.

17. The process of claim 16, wherein the vessels have wall thicknesses of about 0.1 mm.

18. The process of claim 10, wherein the vessels have wall thicknesses of about 0.05 mm to about 0.25 mm.

19. The process of claim 18, wherein the vessels have wall thicknesses of about 0.1 mm.

* * * * *